(12) United States Patent
O'Neill et al.

(10) Patent No.: US 6,723,087 B2
(45) Date of Patent: Apr. 20, 2004

(54) APPARATUS AND METHOD FOR PERFORMING SURGERY ON A PATIENT

(75) Inventors: William G. O'Neill, Maple Grove, MN (US); William Steele, Grand Rapids, MI (US)

(73) Assignee: Medtronic, Inc., Minneapolis, MN (US)

( * ) Notice: Subject to any disclaimer, the term of this patent is extended or adjusted under 35 U.S.C. 154(b) by 114 days.

(21) Appl. No.: 10/017,095

(22) Filed: Dec. 14, 2001

(65) Prior Publication Data

US 2003/0114838 A1 Jun. 19, 2003

(51) Int. Cl.7 ............................................... B25J 11/00
(52) U.S. Cl. ............................................. 606/1; 901/22
(58) Field of Search ............................ 901/22, 37; 606/1

(56) References Cited

U.S. PATENT DOCUMENTS

| | | | | |
|---|---|---|---|---|
| 3,759,563 A | * | 9/1973 | Kitamura | 901/29 |
| 4,721,099 A | * | 1/1988 | Chikama | 600/152 |
| 4,950,273 A | | 8/1990 | Briggs | 606/113 |
| 5,361,583 A | * | 11/1994 | Huitema | 606/131 |
| 5,379,664 A | * | 1/1995 | Kershaw et al. | 901/22 |
| 5,431,645 A | * | 7/1995 | Smith et al. | 606/1 |
| 5,575,799 A | * | 11/1996 | Bolanos et al. | 606/139 |
| 5,807,377 A | * | 9/1998 | Madhani et al. | 606/1 |
| 6,126,651 A | * | 10/2000 | Mayer | 606/1 |
| 6,330,837 B1 | * | 12/2001 | Charles et al. | 901/22 |

FOREIGN PATENT DOCUMENTS

| | | | | |
|---|---|---|---|---|
| EP | 0 646 356 A2 | | 9/1994 | |
| EP | 0646356 A2 | * | 9/1994 | A61B/17/128 |

\* cited by examiner

*Primary Examiner*—Beverly M. Flanagan
(74) *Attorney, Agent, or Firm*—Thomas G. Berry; Daniel W. Latham

(57) ABSTRACT

The invention provides an apparatus and method for performing surgery on a patient. The surgical apparatus includes an input device, at least one hydraulic amplifier operably attached to the input device, and an actuator operably attached to the hydraulic amplifier. Input to the input device is hydraulically modulated via the hydraulic amplifier to manipulate the actuator. The surgical method includes receiving a mechanical input for an action. The mechanical input is hydraulically modulated. The action is controlled based on the hydraulically modulated input.

35 Claims, 5 Drawing Sheets

APPARATUS AND METHOD FOR PERFORMING SURGERY ON A PATIENT

TECHNICAL FIELD OF THE INVENTION

The present invention relates generally to the field of surgery. More particularly, the invention relates to an apparatus and method for performing a hydraulically modulated surgical action for minimally invasive surgery.

BACKGROUND OF THE INVENTION

Recently, there has been a considerable interest in the strategic improvement of traditional surgical methods. Many traditional forms of 'open' surgery may produce significant trauma to the patient because of the need to access and stabilize a surgical site. For example, conventional coronary artery bypass graft (CABG) surgery may involve a medial sternotomy and connection to a heart-lung machine so that the surgeon may work on an exposed and still heart. Because of the trauma, the patient may experience a prolonged recovery time, increased pain and complications, and an overall worsening in prognosis.

Minimally invasive surgery (MIS) is advantageous over traditional forms of 'open' surgery because the overall trauma posed to the patient is reduced. Many 'open' surgeries are now being adapted to be minimally invasive. For example, novel techniques have been developed for performing CABG surgery in a minimally invasive fashion. MIS procedures, such as those used for CABG, typically involve insertion of special surgical instruments such as an endoscope through small incisions in the skin of a patient. The instruments may then be manipulated remotely at the hands of a surgeon. The MIS instruments may perform many of the actions of traditional surgical instruments including grasping objects, suturing, harvesting blood vessels, etc. In this manner, effective MIS may be achieved while reducing many of the deleterious effects associated with 'open' surgery.

One problem associated with MIS instruments, as well as traditional surgical instruments, relates to stability. A certain level of tremor is inherent in the human hand. In many instances, a surgeon's 'steady' hand is needed to effectively perform surgical actions. For example, effective suturing of small blood vessels requires a stable control of the suturing instrument. Many MIS and traditional instruments are not capable of reducing the hand tremor thereby limiting the effectiveness of the tool. Therefore, it would be desirable to effectively reduce the inherent instability associated with hand manipulation of surgical instruments.

Another problem associated with MIS instruments, as well as traditional surgical instruments, relates to precision. For procedures such as minimally invasive CABG, extremely small sutures must be emplaced in various locations proximate the heart. As such, precise control of the motion of the instrument is required. Many traditional instruments do not afford the precision required for such procedures. Therefore, it would be desirable to increase the precision of the surgical instrument. In addition, it may be desirable to perform surgical actions on a minute scale. For such instances, it would be desirable to achieve a level of precision greater than the human hand.

Another problem associated with MIS instruments relates to a limited range of motion. Ideally, the instrument should be able to replicate all of the movements possible (as well as some movements not possible) while in the surgeon's hand. For example, during 'open' surgery, a traditional instrument may be manipulated with six degrees of free movement. During MIS, however, the instruments may be limited to four degrees of free movement or less. This loss of free movement within the surgical site may substantially limit the effectiveness of the procedure to an extent to which it may not be performed in a minimally invasive fashion. As such, it would be desirable for an MIS instrument to have six degrees of free movement.

Therefore, it would be desirable to provide a strategy for performing minimally invasive surgery on a patient that would overcome the aforementioned and other disadvantages.

SUMMARY OF THE INVENTION

One aspect of the present invention provides an apparatus for performing surgery on a patient. The surgical apparatus includes an input device, at least one hydraulic amplifier operably attached to the input device, and an actuator operably attached to the hydraulic amplifier. Input to the input device is hydraulically modulated via the hydraulic amplifier to manipulate the actuator. The input may be provided by a hand of a surgeon. The apparatus may include hydraulic fluid carried by at least one hose for communication between the input device, the at least one hydraulic amplifier, and the actuator. The hydraulic fluid may be a biocompatible fluid such as a saline solution.

The input device may include at least one joystick, lever, dial, and/or button for receiving the input, and an adaptor including at least one hydraulic cylinder operably attached to the at least one joystick, lever, dial, and/or button. The hydraulic cylinder may transmit the received input from the input device. The adaptor may include an adaptor wrist portion, and an adaptor arm portion operably attached to the adaptor wrist portion with a first adaptor ball joint. The adaptor may further include an adaptor sled slidably carried within an adaptor housing and operably attached to the adaptor arm portion with a second adaptor ball joint. An adaptor range of motion of at least one axis of motion may be provided.

The hydraulic amplifier may include a housing including a first opening and a second opening formed therein. The hydraulic amplifier may further include a first amplifier piston slidably carried in the first opening, and a second amplifier piston slidably carried in the second opening. Movement of the first amplifier piston may produce a modulated movement of the second amplifier piston.

The actuator may include at least one gripper, and a manipulator including at least one hydraulic cylinder operably attached to the gripper. The hydraulic cylinder may transmit the modulated input to the gripper for manipulating a surgical instrument operably attached to the actuator. The surgical instrument may include a gripping device, a cutting device, a sealing device, a hemostatic device, a clamping device, a cauterizing device, a suturing device, an ablation device, an anastomotic device, a stabilizing device, a positioning device, a retention device, a video device, a laser device, a harvesting device, an electrical current delivery device, a drug delivery device, a cell delivery device, a gene delivery device, and/or a lead delivery device. The actuator may be manufactured from an injection molded plastic material with an optional insert molded steel material.

The manipulator may include a manipulator wrist portion, and a manipulator arm portion operably attached to the manipulator wrist portion with a first manipulator ball joint. The manipulator may further include a sled slidably carried within a manipulator housing and operably attached to the manipulator arm portion with a second manipulator ball joint. A manipulator range of motion of at least one axis of motion may be provided. The first and second manipulator ball joint may be a spring-loaded joint.

Another aspect of the present invention provides a method for performing surgery on a patient. The surgical method includes receiving a mechanical input for an action. The mechanical input is hydraulically modulated. The action is controlled based on the hydraulically modulated input. Receiving the mechanical input may include translating hand movement of a surgeon. Modulating the mechanical input may include dampening, increasing precision, and increasing a resulting force of the mechanical input. The mechanical input may be transmitted from an input device to a surgical site. The action may be performed on an organ of a patient, such as a beating heart. The action may include gripping, impeding blood flow, clamping, cauterizing, suturing, ablating, joining, sealing, cutting, stabilizing, positioning, retaining, viewing, harvesting, bypassing, delivering an electrical current, delivering a therapeutic agent, delivering a diagnostic agent, delivering a genetic agent, and delivering a cellular agent.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENTS

The present invention is shown and described by the following figures and description of an apparatus and method for performing minimally invasive heart surgery on a patient. Those skilled in the art will recognize that the invention is not limited to the surgical procedure disclosed. For example, the invention may be adapted for use in other minimally invasive and open surgical procedures. In the following description, a side direction (e.g., side view) and a top direction (e.g., top view) are defined as directions orthogonal to one another.

Figure 1:
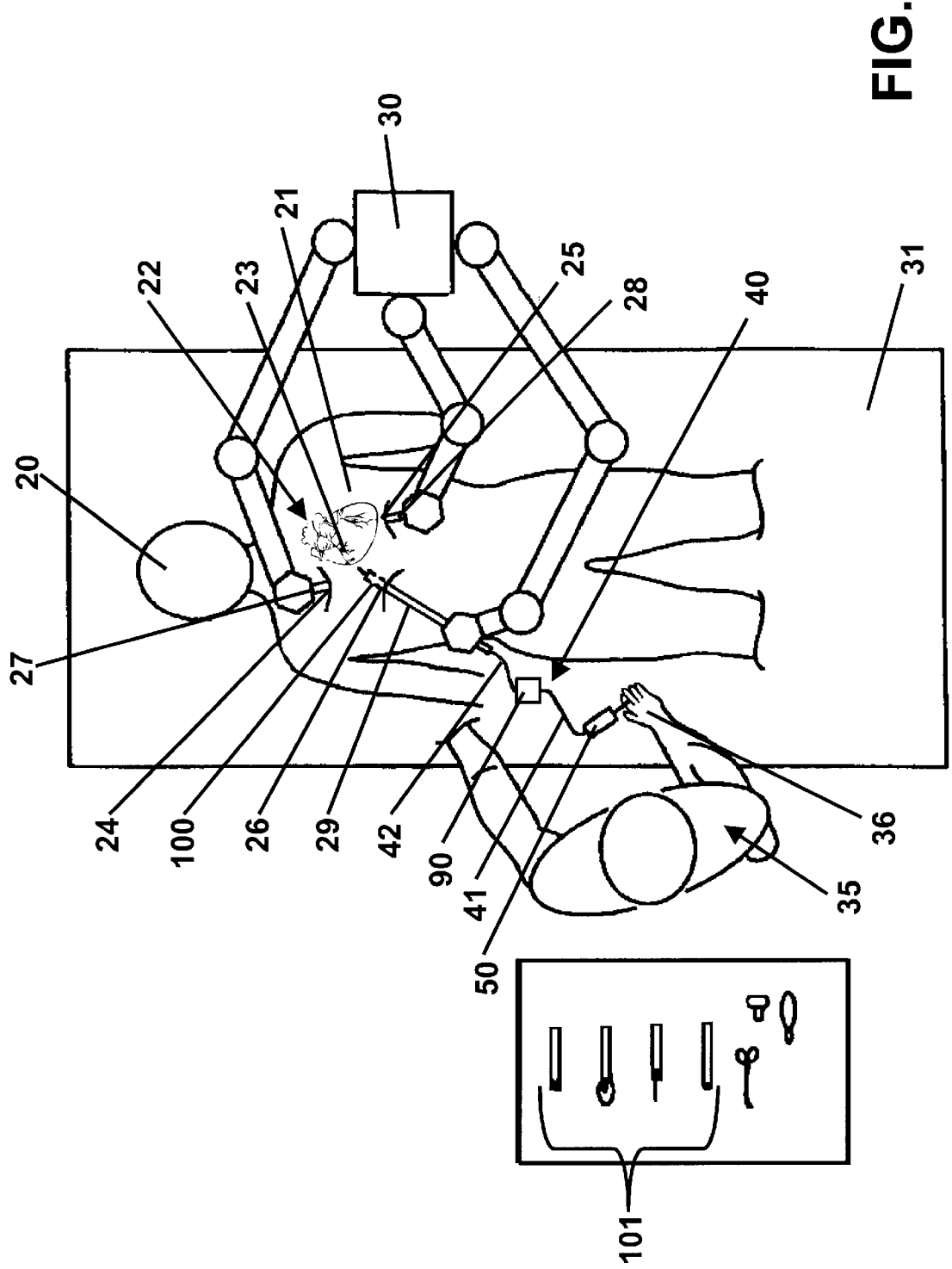
FIG. 1 is a perspective view of a patient undergoing minimally invasive heart surgery.

FIG. 1 is a perspective view of a patient 20 undergoing minimally invasive surgery (MIS), such as a coronary artery bypass graft (CABG) procedure. One or more incisions may be made in the chest wall for surgical access to a thoracic cavity 21, heart 22, and coronary arteries 23. For example, a first incision 24 and a second incision 25 may be positioned at different interstitial rib positions of the patient 20. Furthermore, a third incision 26 may be positioned just below the sternum. A first cannula 27, a second cannula 28, and a third cannula 29 may be inserted through the incisions 24, 25, and 26. The cannulae 27, 28, and 29 may each have a central lumen for allowing surgical instruments to be passed into the thoracic cavity 21.

One or more surgical instruments placed within the cannulae 27, 28, and 29 may be moveably positioned and/or held in place by a manipulator arm device 30, or other such means, recognized in the art. An operator 35, such as a surgeon, may perform the MIS on the patient 20 by manipulating the surgical instruments. The surgical instruments may be a variety of instruments including, but not limited to, imaging devices such as an endoscope (including a laparoscope, arthroscope, hysteroscope, thoracoscope, and the like), and surgical tools. The surgical tools may include a variety of articulated (e.g., jaws, scissors, graspers, clamps, needle holders, micro dissectors, staple appliers, anastomotic device appliers, stabilizers, positioners, manipulators, suction/irrigation tools, clip appliers, and the like) and non-articulated (e.g., cutting blades, cautery probes, catheters, suction/irrigation tools, and the like) devices. Furthermore, the surgical tools may include a surgical apparatus 40 for performing surgery on the patient 20.

The surgical apparatus 40 includes an input device 50, at least one hydraulic amplifier 90 operably attached to the input device 50, and an actuator 100 operably attached to the hydraulic amplifier 90. A first hose 41 or set of hoses may provide communication means between the input device 50 and the at least one hydraulic amplifier 90. A second hose 42 or set of hoses may provide communication means between the at least one hydraulic amplifier 90 and actuator 100. Input to the input device 50 is hydraulically modulated via the at least one hydraulic amplifier 90 to manipulate the actuator 100. The input may be provided to the input device 50 by an operator hand 36. The input device 50 may be positioned at a location suitable for the operator 35 to perform the MIS. In one embodiment, the input device 50 may be positioned proximate to the patient 20 on an operating table 31. In another embodiment, the input device 50 may be positioned at some distance from the patient 20. Preferably, the input device 50 is stabilized to allow for accurate input from the operator hand 36 (i.e., free from external vibrations or movements).

In one embodiment, the actuator 100 may be positioned through the third cannula 29 lumen to access the thoracic cavity 21. During the surgery, the actuator 100 may be passed through any of the cannulae 27, 28, and 29 to permit optimal position. In another embodiment, the actuator 100 may be placed directly through incisions made underneath or between the patient 20 ribs. The operator may manipulate the input device 50 while watching the movements of the slaved actuator 100 with an imaging device (not shown) positioned in the thoracic cavity 21. The imaging device may include a dual camera system providing three dimensional viewing to enhance depth perception during the MIS. The actuator 100 may be replaced during the MIS with replacement actuators 101 to perform various surgical actions.

Figure 2:
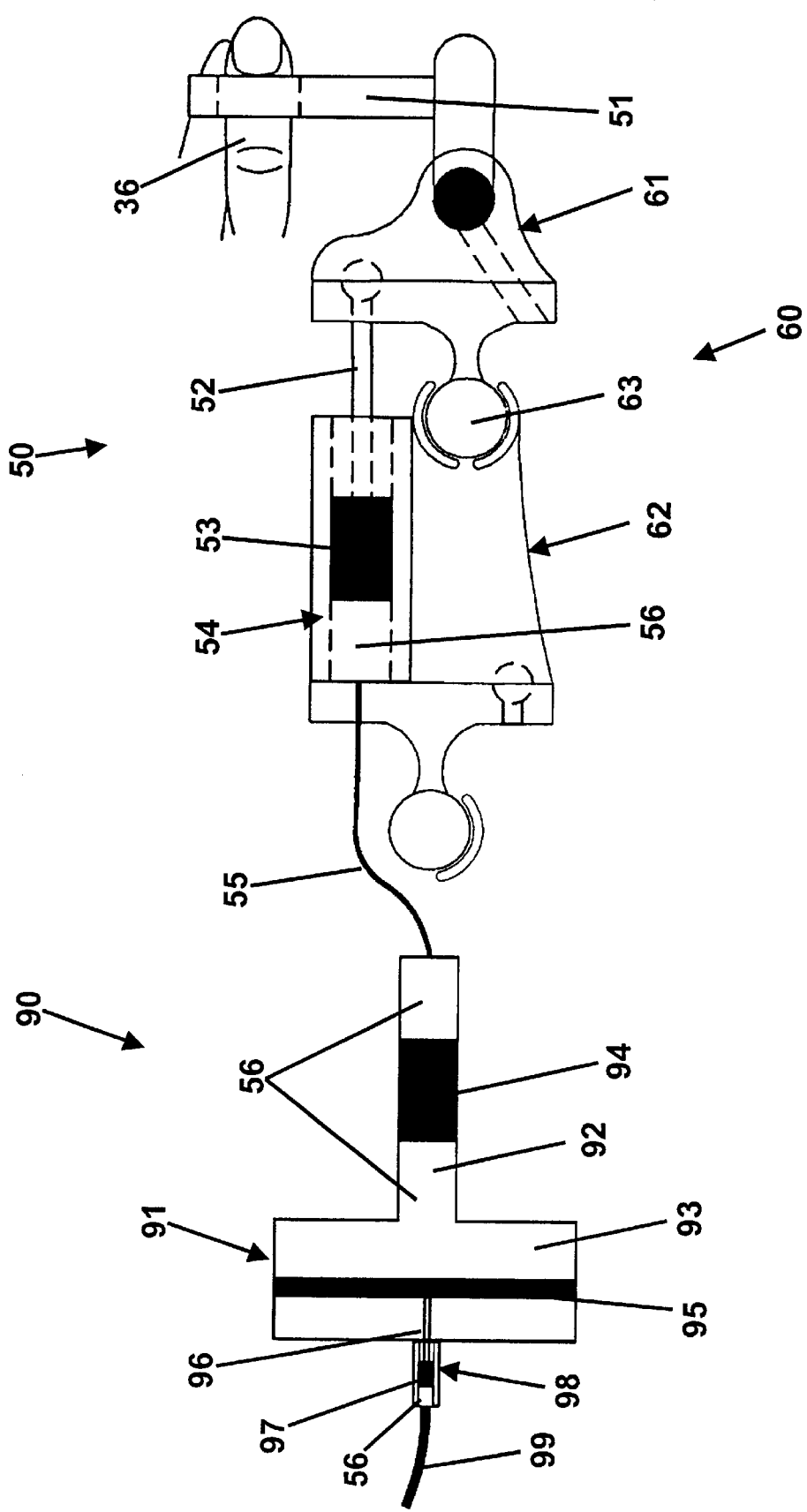
FIG. 2 is a side view of an input device portion operably attached to a hydraulic amplifier made in accordance with the present invention.

FIG. 2 is a side view of an input device 50 portion operably attached to a hydraulic amplifier 90 made in accordance with the present invention. In one embodiment, the input device 50 may include a joystick 51 or other means for receiving the input from the operator hand 36, and an adaptor 60 including at least one hydraulic cylinder operably attached to the joystick 51. In another embodiment, at least one joystick, lever, dial, and/or button may receive input from the operator hand 36. The adaptor 60 may include an adaptor wrist portion 61 attached to an adaptor arm portion 62 with a first adaptor ball joint 63. The adaptor wrist portion 61 may be operably attached to a pushrod 52 coupled to a piston 53. The piston 53 may be slidably carried within a wrist hydraulic cylinder 54. The wrist hydraulic cylinder 54 may transmit the received joystick 51 input from the input device 50 to the hydraulic amplifier 90 through a hose 55. The input may be transmitted by a hydraulic fluid 56 carried within the lumen of the wrist hydraulic cylinder 54, hose 55, and hydraulic amplifier 90. In one embodiment, the hydraulic fluid 56 may be a biocompatible fluid such as a sterile saline solution. Using the biocompatible fluid may reduce deleterious effects to the patient 20 should an accidental leak of one of the hydraulic cylinders or hoses occur.

In one embodiment, the hydraulic amplifier 90 may include a housing 91 including a first opening 92 and a second opening 93 formed therein. The hydraulic amplifier 90 may further include a first amplifier piston 94 slidably carried in the first opening 92, and a second amplifier piston 95 slidably carried in the second opening 93. Furthermore, the second amplifier piston 95 may be operably attached to a pushrod 96 and third amplifier piston 97 carried within an amplifier hydraulic cylinder 98. Movement of the first amplifier piston 94 may produce a modulated movement of the second amplifier piston 95. Furthermore, movement of the second amplifier piston 95 produces movement of the third amplifier piston 97 thereby moving hydraulic fluid 56 within a hose 99. The hose 99 operably connects the hydraulic amplifier 90 to an actuator (not shown).

Figure 3:
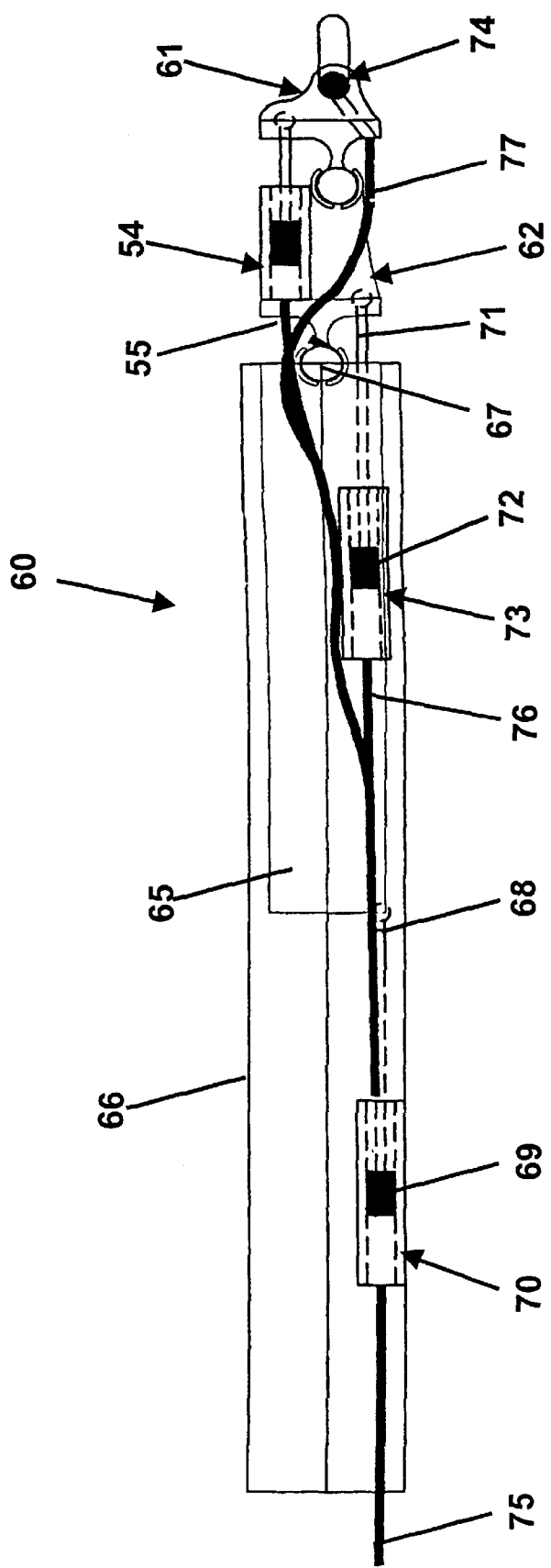
FIG. 3 is a side view of an adaptor made in accordance with the present invention.

FIG. 3 is a side view of the adaptor 60 shown in FIG. 2 further including an adaptor sled 65 slidably carried within an adaptor housing 66. The adaptor sled 65 may be operably attached to the adaptor arm portion 62 with a second adaptor ball joint 67. Furthermore, the adaptor sled 65 may be operably attached to a pushrod 68 and piston 69 carried in a sled hydraulic cylinder 70. The adaptor arm portion 62 may be operably attached to a pushrod 71 and piston 72 slidably carried in an arm hydraulic cylinder 73. A finger hydraulic cylinder 74 carrying a slidable piston (not shown) may be positioned in the adaptor wrist portion 61. The wrist hydraulic cylinder 54, the sled hydraulic cylinder 70, arm hydraulic cylinder 73, and finger hydraulic cylinder 74 may each be connected to a hose 55, 75, 76, and 77. The hoses 55, 75, 76, and 77 may also be each connected to individual hydraulic amplifiers (not shown). The hydraulic cylinders 54, 70, 73, and 74 and their respective hoses 55, 75, 76, and 77 may each carry hydraulic fluid. Piston movement within the hydraulic cylinders 54, 70, 73, and 74 forces the hydraulic fluid to flow between its piston and respective hydraulic amplifier through the hosing 55, 75, 76, and 77.

Figure 4:
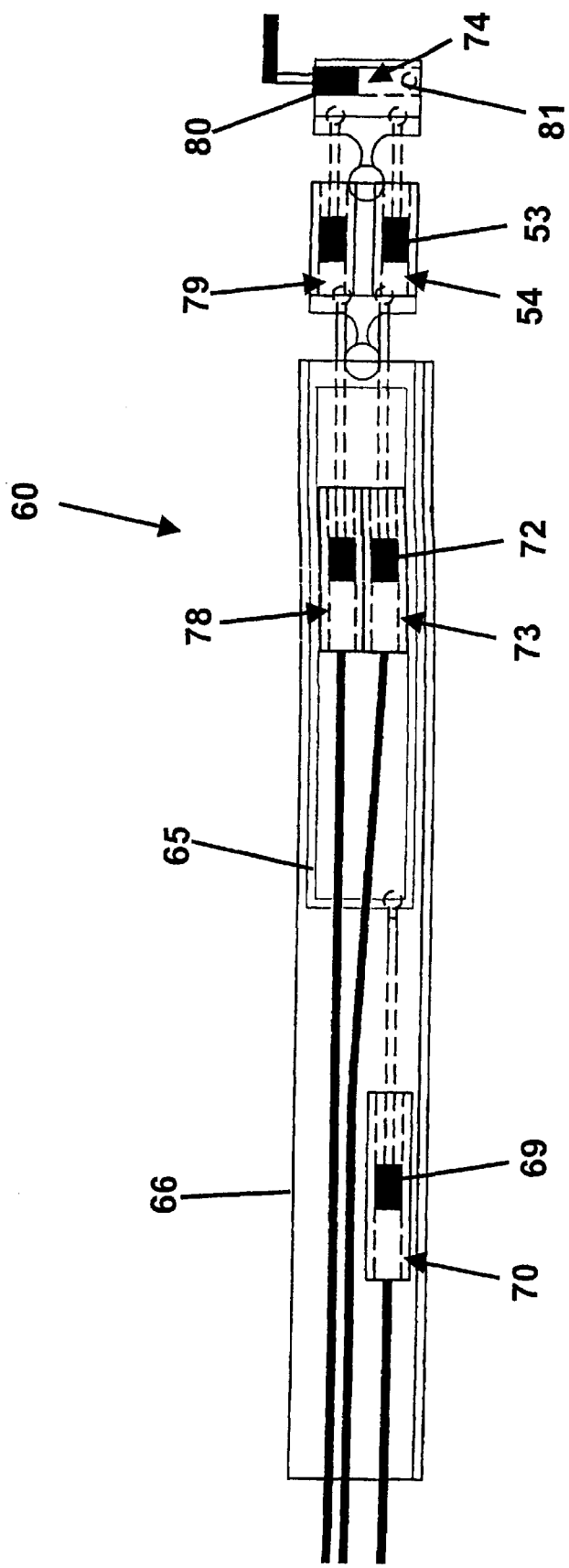
FIG. 4 is a top view of the adaptor shown in FIG. 3.

In the described embodiment, a total of six hydraulic cylinders are provided. As shown in FIG. 4, a top view of the adaptor 60 reveals two hydraulic cylinders obscured from view in FIG. 3. For example, another arm hydraulic cylinder 78 and wrist hydraulic cylinder 79 are provided; each cylinder 78, 79 also includes an associated piston, pushrod, and hose. The arm hydraulic cylinders 73, 78 may be attached to the adaptor sled 65. Furthermore, the sled hydraulic cylinder 70 may be attached to the adaptor housing 66. FIG. 4 also shows an alternative view of the finger hydraulic cylinder 74 revealing the position of its piston 80 and point of hose attachment 81. Of note, the finger hydraulic cylinder 74 does not contain a pushrod.

Figure 5:
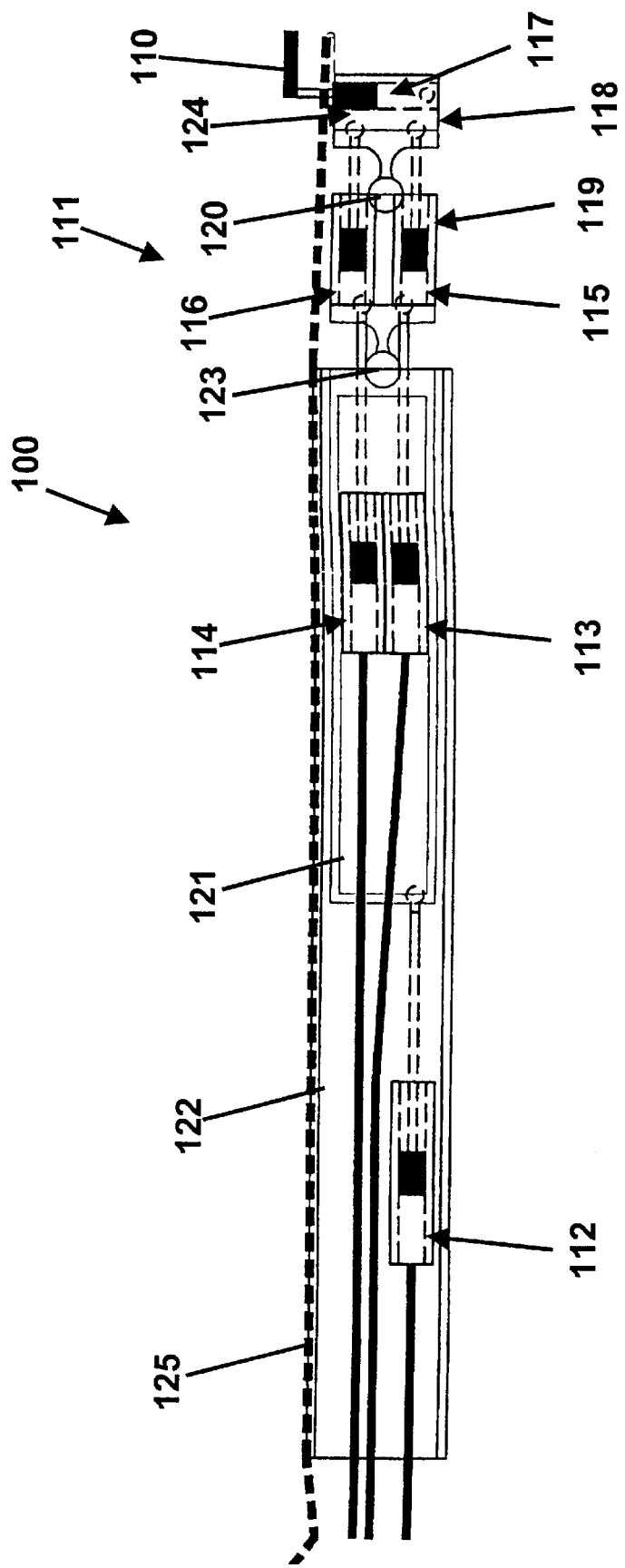
FIG. 5 is a top view of an actuator made in accordance with the present invention.

FIG. 5 is a top view of an actuator 100 made in accordance with the present invention. In one embodiment, the actuator 100 includes a gripper 110, and a manipulator 111 including six hydraulic cylinders 112, 113, 114, 115, 116, and 117 operably attached to the gripper 110. The manipulator 111 may share many structural elements with the input device adaptor. The manipulator 111 may include a manipulator wrist portion 118, operably attached to a manipulator arm portion 119 with a first manipulator ball joint 120. The manipulator 111 may further include a manipulator sled 121 slidably carried within a manipulator housing 122. The manipulator sled 121 may be operably attached to the manipulator arm portion 119 with a second manipulator ball joint 123. The first 120 and second 123 manipulator ball joints may be spring-loaded joints.

As with the input device, individual hydraulic amplifiers (not shown) may be operably connected to each of the manipulator hydraulic cylinders 112, 113, 114, 115, 116, and 117 with hoses. In addition, each manipulator hydraulic cylinder 112, 113, 114, 115, 116, and 117 may be in communication with an analogous adaptor hydraulic cylinder. The manipulator hydraulic cylinders 112, 113, 114, 115, 116, and 117 may transmit the modulated input received from the hydraulic amplifiers to the gripper 110 for manipulating a surgical instrument. The surgical instrument may include a gripping device, a cutting device, a sealing device, a hemostatic device, a clamping device, a cauterizing device, a suturing device, an ablation device, an anastomotic device, a stabilizing device, a positioning device, a retention device, a video device, a laser device, a harvesting device, an electrical current delivery device, a drug delivery device, a gene delivery device, a cell delivery device, a gene delivery device, and/or a lead delivery device. For example, an ablation device 124 and wire 125 for providing electrical current are shown mounted on the actuator 100.

The manipulator 111 may be structurally similar to the adaptor 60, except for their scale. As such, the actuator 100 may have dimensions small enough to allow it to pass through a small (e.g., about 15 mm diameter or less) port, such as a cannula lumen. The input device 50 may have dimensions for receiving input from a human hand, that is, about 10 to 50 cm in length. The input device 50 and hydraulic amplifier 90 may be manufactured from a sufficiently rigid material such as stainless steel, plastic, polysulfone, polycarbonate, and the like. The input device 50 and hydraulic amplifier 90 may be flash steam sterilized and reused after a surgical procedure. The input device 50 or portions thereof may be disposable. Portions of the actuator 100 may be manufactured from an injection molded plastic material. A potential problem with the use of a plastic material relates to controlling tight tolerances of the injection-molded joints. Slop or play in the joints due to tolerance gaps may impede the intended precision of the actuator 100. Therefore, the joints may be spring loaded to eliminate slop and play. Such anti-backlash gears are known in the art. Another potential problem with the use of the plastic material relates to a stiffness required for some surgical actions. To increase the stiffness, the actuator 100 may include rods manufactured from a rigid material, such as stainless steel. The rods may be insert molded into the plastic components. The actuator 100 may be disposable, sterilized and stored in sterile packing and then disposed after use. Alternatively, the actuator 100 may be reused following a sterilization procedure. The input device 50, hydraulic amplifier 90, and actuator 100 pistons may be manufactured from an elastomeric material such as plastic or rubber. Preferably, the pistons form a sealed but slidable interface with its hydraulic cylinder, much like that with a syringe. A small amount of lubricating fluid (e.g., silicone oil) may be applied to lower frictional forces. The piston pushrods may be fabricated from a sufficient rigid material, such as stainless steel, providing a high stiffness to size ratio. Those skilled in the art will recognize that the aforementioned sizes, materials, and configurations may be varied while retaining many of the characteristics of the surgical apparatus 40.

Referring collectively now to FIGS. 1–4, in which like elements have like reference numbers, the surgical apparatus may be used to perform a surgical action during minimally invasive surgery. In one embodiment, the operator 35 (e.g., surgeon) may provide the mechanical input with operator hand 36 movements. The input may be received by the input device 50, specifically, through joystick 51 movements of the adaptor 60. The adaptor 60 may be designed to follow the operator hand 36 movements. More specifically, the adaptor 60 may be designed to translate operator hand 36 movements through an adaptor range of motion of at least one axis of motion. In one embodiment, the adaptor 50 may be capable of translating six degrees of motion. In another embodiment, the adaptor 50 may be capable of translating more or less than six degrees of motion.

In one embodiment, the adaptor hydraulic cylinders 54, 70, 73, 74, 78, and 79, ball joints 63, 67, and sled 65 may provide means for receiving and translating the mechanical input. As the joystick 51 is moved in a first movement (e.g., a side motion), the finger hydraulic cylinder piston 80 moves along an axis thereby providing a first degree of motion. In a second movement (e.g., a finger motion), the adaptor wrist portion 61 moves along two axes facilitated by the first adaptor ball joint 63. The wrist hydraulic cylinders 54, 79 then "read" the adaptor wrist portion 118 motions; the diametrically opposed position of the wrist hydraulic cylinders 54, 75 makes this possible. For example, movement of the adaptor wrist portion 61 through a circular range of motion allowed by the first adaptor ball joint 63 pushes and pulls the attached pushrods 52. Movement of the adaptor wrist portion 61 in one axis (e.g., side to side) pushes one pushrod 52 while pulling the other. Movement of the adaptor wrist portion 61 in an orthogonal axis (e.g., up and down) either pushes both pushrods 52 or pulls both pushrods 52. In this manner, the wrist hydraulic cylinder 54, 79 pair receives and translates operator hand 36 movement input in two axes. As such, the wrist hydraulic cylinders 54, 79 provide a second and third degree of motion.

In a third movement (e.g., a wrist motion), the adaptor arm portion 62 moves along two axes facilitated by the second adaptor ball joint 67. As with the wrist hydraulic cylinders 54, 79, the arm hydraulic cylinders 73, 78 then "read" the adaptor arm portion 62 motions. As such, the diametrically opposed arm hydraulic cylinders 73, 78 provide a fourth and fifth degree of motion. In a fourth movement (e.g., an arm motion), the adaptor sled 65 slides within the adaptor housing 66 along an axis thereby providing a sixth degree of motion. The sled hydraulic cylinder piston 69 is forcibly moved during this movement as its pushrod 68 is attached to the adaptor sled 65.

After the input has been received and translated, it may then be transmitted to at least one hydraulic amplifier 90. In one embodiment, the adaptor hydraulic cylinders 54, 70, 73, 74, 78, and 79, hydraulic fluid 56, and tubes 55, 75, 76, and 77 (not all shown) may provide means for transmitting the mechanical input. For example, as an input force acts upon a hydraulic cylinder piston, hydraulic fluid is forced into and out of the cylinder. The hydraulic fluid is then forced through a hose thereby transmitting the input force to a hydraulic cylinder. In one embodiment, each adaptor hydraulic cylinder 54, 70, 73, 74, 78, and 79 is coupled to an individual hydraulic amplifier 90. In another embodiment, some or combinations of the adaptor hydraulic cylinders 54, 70, 73, 74, 78, and 79 are coupled to individual hydraulic amplifiers 90. In another embodiment, some of the adaptor hydraulic cylinders 54, 70, 73, 74, 78, and 79 may be coupled directly to actuator hydraulic cylinders 112, 113, 114, 115, 116, and 117.

Once the mechanical input is transmitted to the hydraulic amplifier 90, the input is hydraulically modulated. For example, movement of the first amplifier piston 84 may produce a modulated movement of the second amplifier piston 85. In one embodiment, the modulated movement may include a reduced motion wherein the mechanical input is reduced with respect to translation. The geometry of the first and second openings 92, 93 governs the reduction:

$$\text{Volume}=A_1*X_1=A_2*X_2$$

The first opening 92 may have a radius ($r_1$) and an area ($A_1$) wherein $A_1=\pi*r_1^2$. Similarly, the second opening 93 a diameter ($r_2$) and area ($A_2$) wherein $A_2=\pi*r_2^2$. The first and second amplifier pistons 94, 95 may have a linear translation along an axis ($X_1$ and $X_2$, respectively). Assuming the volume of the hydraulic fluid 56 transferred remains constant, translation $X_2$ is one-fifth of $X_1$, if for example, $A_2$ is five times greater than $A_1$. In this example, movement of the first amplifier piston 94 results in a reduced movement of the second piston 95 by a fifth. The reduced motion may provide an increased precision of the surgical action since the input is modulated into finer, more precise output actions. In addition, the reduced motion may provide dampening of undesirable movements (e.g., shaking and tremors) thereby reducing the inherent instability associated with hand manipulation of the surgical instrument. In another embodiment, the modulated movement may include an increased motion wherein the mechanical input is increased with respect to translation. This may be achieved when $A_1$ is greater than $A_2$.

The modulated movement may also include an amplified force wherein the mechanical input force is increased at the expense of translational distance. The geometry of the first and second openings 92, 93 governs the amplification:

$$\text{Pressure}=F_1/A_1=F_2/A_2$$

The first and second openings 92, 93 may have area ($A_1$) and area ($A_2$), respectively. Assuming the internal pressure within the first opening 92 and second opening 93 remains constant, $F_2=A_2/A_1*F_1$. Using the previous example, a five-fold ratio of $A_2/A_1$ amplifies the force by five-fold. As such, a 1 lb. input force would result in 5 lbs. of output force, minus frictional loss. The amplified force may enhance the stiffness of the small actuator 100 while helping to overcome the frictional losses inherent with moving interfaces.

After the mechanical input has been modulated, movement of the second amplifier piston 95 may forcibly move the pushrod 96 and third amplifier piston 97. The modulated input may then be hydraulically transmitted to the actuator 100 through the hose 99. Additionally, some input received by the input device 50 may be transmitted directly to the actuator 100, bypassing the hydraulic amplifier 90. In one embodiment, the manipulator 111 is structurally similar to the adaptor 60 (except for scale). Therefore, the manipulator 111 and adaptor 60 function in an analogous fashion.

The adaptor hydraulic cylinders 54, 70, 73, 74, 78, and 79 may each be coupled to a corresponding manipulator hydraulic cylinder 112, 113, 114, 115, 116, and 117 to provide analogous movements. For example, the adaptor wrist hydraulic cylinder 54 may be coupled to the manipulator wrist hydraulic cylinder 115. Joystick 51 movements may be transmitted to and replicated at the gripper 110 (with optional modulation) using coupled hydraulic cylinders. As such, the manipulator 111 may be designed to replicate operator hand 36 movements through a manipulator range of motion of at least one axis of motion. In one embodiment, the manipulator 111 may be capable of translating six degrees of motion. Providing six degrees of motion may increase the effectiveness of the surgical apparatus 40. As such, the apparatus 40 may perform many of the actions of traditional surgical instruments (e.g., grasping objects, suturing, harvesting blood vessels, etc.). Some MIS actions, however, may require different degrees of motion. Thus, in another embodiment, the manipulator 111 may be capable of translating different motions than the six degrees of motion provided in the described embodiment. This may be accomplished by rearranging, modifying, adding, or removing input device, hydraulic amplifier, and actuator components (e.g., hydraulic cylinders, ball joints, amplifier opening sizes, component geometries and sizes, etc.)

The actuator 100 may then perform a controlled action at a surgical site (e.g., thoracic cavity 21) based on the mechanical input. The action may include gripping, impeding blood flow, clamping, cauterizing, suturing, ablating, joining, sealing, cutting, stabilizing, positioning, retaining, viewing, harvesting, bypassing, delivering an electrical current, delivering a therapeutic agent, delivering diagnostic agent, delivering a genetic agent, and delivering a cellular agent. The action may be determined by the configuration of the actuator 100. For example, mounting the ablation device 124 and wire 125 on the actuator 100 provides means for ablating tissue. In one embodiment, the action may be performed during a minimally invasive CABG procedure on coronary arteries 23 (e.g., creation of an anastomosis). In addition, the action may include harvesting an interior mammary artery (IMA) used during the CABG procedure. In another embodiment, a portion on the actuator 100 may be stabilized on a beating heart 22 to perform the action. In another embodiment, a portion of the actuator 100 may be used to stabilize a portion of a beating heart 22. In another embodiment, a portion of the actuator 100 may be used to position a beating heart 22. The actuator 100 may be stabilized to the heart 22 according to procedures known in the art. Allowing the heart 22 to beat during a cardiac procedure may eliminate the need for placing the patient 20 on a heart-lung machine thereby reducing overall trauma. Thus, the patient 20 may experience shortened recovery time, decreased pain and complications, and an overall improvement in prognosis.

While the embodiments of the invention disclosed herein are presently considered preferred, various changes and modifications can be made without departing from the spirit and scope of the invention. Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

What is claimed is:

1. An apparatus for performing heart surgery on a patient comprising:
    an input device including an adaptor wrist portion rotably attached to an adaptor arm portion, and a slidable sled rotably attached to the adaptor arm portion;
    at least one hydraulic amplifier operably attached to the input device; and
    an actuator operably attached to the hydraulic amplifier; wherein the input to the input device is hydraulically modulated via the hydraulic amplifier to manipulate the actuator.

2. The apparatus of claim 1 wherein each rotable attachment comprises a ball joint.

3. The apparatus of claim 1 further comprising hydraulic fluid for communication between the hydraulic amplifier and at least one of the input device and the actuator.

4. The apparatus of claim 3 wherein the hydraulic fluid comprises a biocompatible fluid.

5. The apparatus of claim 1 wherein the input device comprises:
    a joystick for receiving the input; and
    at least one hydraulic cylinder operably attached to the joystick and integral to the adaptor, wherein the hydraulic cylinder transmits the received joystick input from the input device.

6. The apparatus of claim 1 wherein an adaptor range of motion is provided comprising at least one axis of motion.

7. The apparatus of claim 1 wherein the hydraulic amplifier comprises:
    a housing including a first opening and a second opening formed therein;
    a first amplifier piston slidably carried in the first opening; and
    a second amplifier piston slidably carried in the second opening, wherein movement of the first amplifier piston produces a modulated movement of the second amplifier piston.

8. The apparatus of claim 1 wherein the actuator comprises:
    at least one gripper; and
    a manipulator including at least one hydraulic cylinder operably attached to the gripper, wherein the hydraulic cylinder transmits the modulated input to the gripper for manipulating a surgical instrument.

9. The apparatus of claim 8 wherein the surgical instrument is selected from a group consisting of a gripping device, a hemostatic device, a cauterizing device, a suturing device, an ablation device, an anastomtic device, a stabilizing device, a retention device, a video device, a laser device, a harvesting device, and a current delivery device.

10. The apparatus of claim 8 wherein the actuator comprises an injection molded plastic material.

11. The apparatus of claim 10 wherein the injected molded plastic material comprises an insert molded steel material.

12. The apparatus of claim 8 wherein the manipulator comprises:
    a manipulator wrist portion;
    a manipulator arm portion operably attached to the manipulator wrist portion with a first manipulator ball joint; and
    a sled slidably carried within a manipulator housing and operably attached to the manipulator arm portion with a second manipulator ball joint, wherein a manipulator range of motion is provided.

13. The apparatus of claim 12 wherein the manipulator range of motion comprises at least one axis of motion.

14. The apparatus of claim 12 wherein at least one of the first manipulator ball joint and the second manipulator ball joint comprises a spring loaded joint.

15. A method of performing heart surgery on a patient comprising:

receiving a mechanical input for an action by an adaptor;

transmitting the mechanical input from the adaptor;

providing an adaptor range of motion;

hydraulically modulating the mechanical input;

controlling the action based on the hydraulically modulated input with a manipulator; and providing a manipulator range of motion that corresponds to the adaptor range of motion.

16. The method of claim 15 wherein receiving the mechanical input comprises translating a surgeon hand movement.

17. The method of claim 15 wherein modulating the mechanical input comprises dampening the mechanical input.

18. The method of claim 15 wherein modulating the mechanical input comprises increasing precision of the mechanical input.

19. The method of claim 15 wherein modulating the mechanical input comprises increasing a resulting force of the mechanical input.

20. The method of claim 15 wherein the action is performed on a beating heart.

21. The method of claim 15 wherein the action is performed on a coronary artery.

22. The method of claim 15 wherein the action is selected from a group consisting of gripping, impeding blood flow, clamping, cauterizing, suturing, ablating, joining, cutting, stabilizing, retaining, viewing, harvesting, bypassing, and delivering an electrical current.

23. An apparatus for performing heart surgery on a patient comprising:

an input device;

at least one hydraulic amplifier operably attached to the input device; and an actuator operably attached to the hydraulic amplifier, wherein input to the input device is hydraulically modulated via the hydraulic amplifier to manipulate the actuator, the actuator including a manipulator wrist portion rotably attached, a manipulator arm portion, and a slidable sled attached to the arm portion.

24. The apparatus of claim 23 further comprising hydraulic fluid for communication between the hydraulic amplifier and at least one of the input device and the actuator.

25. The apparatus of claim 24 wherein the hydraulic fluid comprises a biocompatible fluid.

26. The apparatus of claim 23 wherein the input device comprises:

a joystick for receiving the input; and an adaptor including at least one hydraulic cylinder operably attached to the joystick, wherein the hydraulic cylinder transmits the received joystick input from the input device.

27. The apparatus of claim 26 wherein the adaptor comprises:

an adaptor wrist portion;

an adaptor arm portion operably attached to the adaptor wrist portion with a first adaptor ball joint; and an adaptor sled slidably carried within an adaptor housing and operably attached to the adaptor arm portion with a second adaptor ball joint, wherein an adaptor range of motion is provided.

28. The apparatus of claim 27 wherein the adaptor range of motion comprises at least one axis of motion.

29. The apparatus of claim 23 wherein the hydraulic amplifier comprises:

a housing including a first opening and a second opening formed therein;

a first amplifier piston slidably carried in the first opening; and a second amplifier piston slidably carried in the second opening, wherein movement of the first amplifier piston produces a modulated movement of the second amplifier piston.

30. The apparatus of claim 23 wherein the actuator comprises:

at least one gripper; and at least one hydraulic cylinder operably attached to the gripper, wherein the hydraulic cylinder transmits the modulated input to the gripper for manipulating a surgical instrument.

31. The apparatus of claim 30 wherein the surgical instrument is selected from a group consisting of a gripping device, a hemostatic device, a cauterizing device, a suturing device, an ablation device, an anastomotic device, a stabilizing device, a retention device, a video device, a laser device, a harvesting device, and a current delivery device.

32. The apparatus of claim 23 wherein the actuator comprises an injection molded plastic material.

33. The apparatus of claim 32 wherein the injected molded plastic material comprises an insert molded steel material.

34. The apparatus of claim 23 wherein the manipulator range of motion comprises at least one axis of motion.

35. The apparatus of claim 23 wherein each rotable attachment comprises a ball joint.

* * * * *